(12) United States Patent
Yamate

(10) Patent No.: US 11,834,390 B2
(45) Date of Patent: Dec. 5, 2023

(54) ADHESIVE COMPOSITION

(71) Applicant: NIPPON SODA CO., LTD., Tokyo (JP)

(72) Inventor: Taiki Yamate, Ichihara (JP)

(73) Assignee: NIPPON SODA CO., LTD., Tokyo (JP)

(*) Notice: Subject to any disclaimer, the term of this patent is extended or adjusted under 35 U.S.C. 154(b) by 276 days.

(21) Appl. No.: 17/280,931

(22) PCT Filed: Oct. 2, 2019

(86) PCT No.: PCT/JP2019/039008
§ 371 (c)(1),
(2) Date: Mar. 29, 2021

(87) PCT Pub. No.: WO2020/071456
PCT Pub. Date: Apr. 9, 2020

(65) Prior Publication Data
US 2021/0347726 A1    Nov. 11, 2021

(30) Foreign Application Priority Data
Oct. 5, 2018  (JP) ................................. 2018-190398

(51) Int. Cl.
| C07C 233/09 | (2006.01) |
| C09D 133/26 | (2006.01) |
| C09D 5/00 | (2006.01) |
| C09J 133/26 | (2006.01) |

(52) U.S. Cl.
CPC ............ *C07C 233/09* (2013.01); *C09D 5/002* (2013.01); *C09D 133/26* (2013.01); *C09J 133/26* (2013.01)

(58) Field of Classification Search
CPC .... C07C 233/09; C09D 5/002; C09D 133/26; C09J 133/26
See application file for complete search history.

(56) References Cited

U.S. PATENT DOCUMENTS

2015/0353738 A1    12/2015  Yamate

FOREIGN PATENT DOCUMENTS

| CN | 109305925 A | 2/2019 | |
| EP | 3 527 642 A1 | 8/2019 | |
| GB | 2102426 A * | 2/1983 | ............... C07C 1/00 |
| JP | H09221520 A * | 8/1997 | ............. C08F 20/54 |
| JP | 2004-269676 A | 9/2004 | |
| JP | 2018-28603 A | 2/2018 | |
| WO | 2014/115210 A1 | 7/2014 | |
| WO | 2018/070079 A1 | 4/2018 | |
| WO | 2019/198792 A1 | 10/2019 | |

OTHER PUBLICATIONS

Machine translation of JP H09221520 A (Year: 1997).*
Machine Translation of WO 2019/198792 A1 (Year: 2019).*
Dec. 3, 2019 International Search Report issued in International Patent Application No. PCT/JP2019/039008.
Sep. 22, 2022 Office Action issued in Indian Patent Application No. 202147012399.

* cited by examiner

*Primary Examiner* — Callie E Shosho
*Assistant Examiner* — Bethany M Miller
(74) *Attorney, Agent, or Firm* — Oliff PLC

(57) ABSTRACT

An adhesive composition having excellent adhesive properties and adhesiveness to a variety of plastics such as polypropylene, polyethylene, or a cycloolefin resin. The adhesive composition includes a polymer having a repeating unit derived from a polymerizable compound of the following formula (I):

$$X^1 \underset{(R)_{m1}}{\underset{|}{\bigcirc}} Z^1 \underset{Y}{\overset{|}{N}} Z^2 \underset{(R)_{m2}}{\underset{|}{\bigcirc}} (X^2)_n \quad (I)$$

in which $X^1$ and $X^2$ each independently represent a C7 to C20 alkyl group or a C7 to C20 alkoxy group; n represents 0 or 1; $Z^1$ and $Z^2$ each independently represent a single bond or a C1 to C3 alkylene group; R each independently represents an organic group or a halogeno group; m1 and m2 each independently represent any integer of 0 to 4; and Y represents a polymerizable functional group.

13 Claims, No Drawings

ADHESIVE COMPOSITION

TECHNICAL FIELD

The present invention relates to a novel adhesive composition, particularly an adhesive composition having excellent adhesive properties and adhesiveness to a plastic substrate and an adhesive composition that may be used as a coating agent or an adhesive. This application claims priority to Japanese Patent Application No. 2018-190398, filed on Oct. 5, 2018, the contents of which are incorporated herein.

BACKGROUND ART

Patent Document 1 discloses that adhesive compositions using a polymer of N,N-diphenylacrylamide are used as coating agents having excellent adhesive properties and adhesiveness to a cycloolefin resin. This document discloses only a C1 to C6 alkyl group, specifically methyl group, as an alkyl group that is a substituent for a phenyl group of the above N,N-diphenylacrylamide, and not long-chain alkyl groups having 7 or more carbon atoms.

PRIOR ART DOCUMENTS

Patent Documents

Patent Document 1: WO2018/070079

SUMMARY OF THE INVENTION

Object to be Solved by the Invention

However, given that these adhesive compositions do not have adequate adhesive properties to polyethylene or polypropylene, their adhesive properties need to be improved to be used for these substrates.

Means to Solve the Object

The present inventor has studied diligently in order to achieve the above object, and as a result found that a polymer having a repeating unit derived from a polymerizable compound of N,N-diphenylacrylamide substituted by a C7 to C20 alkyl chain or the like exhibits adhesive properties and adhesiveness to a variety of plastics including polyethylene and polypropylene, leading to the completion of the present invention.

That is, the present invention relates to the following inventions.

(1) An adhesive composition, comprising a polymer having a repeating unit derived from a polymerizable compound of formula (I):

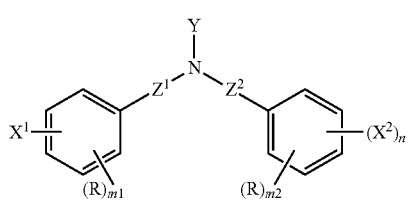

(wherein $X^1$ and $X^2$ each independently represent a C7 to C20 alkyl group or a C7 to C20 alkoxy group; n represents 0 or 1; $Z^1$ and $Z^2$ each independently represent a single bond or a C1 to C3 alkylene group; R each independently represents an organic group or a halogeno group; m1 and m2 each independently represent any integer of 0 to 4; and Y represents a polymerizable functional group).

(2) The adhesive composition according to (1), wherein in formula (I), Y is an acryloyl group or a methacryloyl group.

(3) The adhesive composition according to (1) or (2), wherein the polymerizable compound of formula (I) is a compound of formula (II):

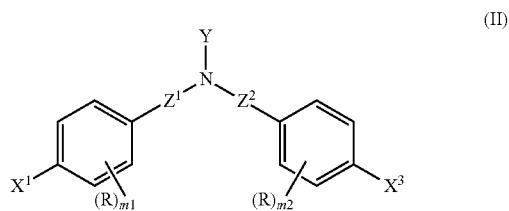

(wherein $X^1$ represents a C7 to C20 alkyl group or a C7 to C20 alkoxy group; $X^3$ represents a C7 to C20 alkyl group, a C7 to C20 alkoxy group, a hydrogen atom, an organic group, or a halogeno group; $Z^1$ and $Z^2$ each independently represent a single bond or a C1 to C3 alkylene group; R each independently represents an organic group or a halogeno group; m1 and m2 each independently represent any integer of 0 to 4; and Y represents a polymerizable functional group).

(4) The adhesive composition according to any one of (1) to (3), wherein the C7 to C20 alkyl group and the C7 to C20 alkoxy group are branched.

(5) The adhesive composition according to any one of (1) to (4), wherein the adhesive composition is an adhesive composition for a plastic substrate.

(6) The adhesive composition according to (5), wherein the plastic substrate is a polyolefin substrate.

(7) The adhesive composition according to (5), wherein the plastic substrate is a polypropylene substrate or a polyethylene substrate.

(8) The adhesive composition according to (5), wherein the adhesive composition is a coating agent.

(9) The adhesive composition according to (8), wherein the coating agent is a primer.

(10) The adhesive composition according to (5), wherein the adhesive composition is an adhesive.

(11) A compound of formula (I):

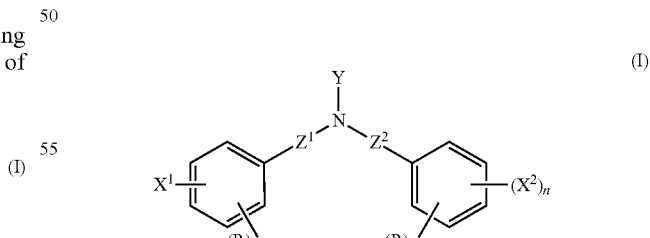

(wherein $X^1$ and $X^2$ each independently represent a C7 to C20 alkyl group or a C7 to C20 alkoxy group; n represents 0 or 1; $Z^1$ and $Z^2$ each independently represent a single bond or a C1 to C3 alkylene group; R each independently represents an organic group or a halogeno group; m1 and m2 each independently represent any integer of 0 to 4; and Y represents a polymerizable functional group).

(12) A polymer having a repeating unit derived from a polymerizable compound of formula (I):

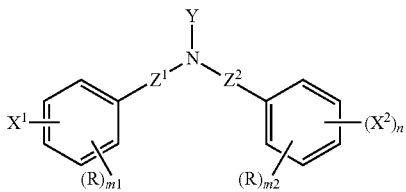

(wherein $X^1$ and $X^2$ each independently represent a C7 to C20 alkyl group or a C7 to C20 alkoxy group; n represents 0 or 1; $Z^1$ and $Z^2$ each independently represent a single bond or a C1 to C3 alkylene group; R each independently represents an organic group or a halogeno group; m1 and m2 each independently represent any integer of 0 to 4; and Y represents a polymerizable functional group).

Effect of the Invention

A coating film having excellent adhesive properties and adhesiveness to a plastic substrate, particularly a substrate of a polyolefine such as polycycloolefin, polyethylene, or polypropylene may be formed by using the adhesive composition of the present invention. Conventionally, there has been no adhesive composition that may be widely used for substrates of these various plastics, but the adhesive composition of the present invention may be used in that way. A functional film that may not be conventionally directly formed on a plastic substrate may be laminated via a coating film of the present invention. Further, plastic substrates, including the above substrates, may be adhered together via a coating film.

Since the surface of a plastic substrate does not need to be modified by UV-ozone treatment or the like by using the adhesive composition of the present invention, the original characteristics of the plastic substrate may be maintained. In addition, a variety of adhesive compositions are easily prepared because the adhesive composition of the present invention is highly soluble in a solvent or a resin.

Additionally, the adhesive composition of the present invention may also be used as an adhesive.

MODE OF CARRYING OUT THE INVENTION

1. Adhesive Composition
[Polymer]

The adhesive composition of the present invention comprises a polymer having a repeating unit derived from a polymerizable compound of formula (I) (occasionally called "polymer (I)".).

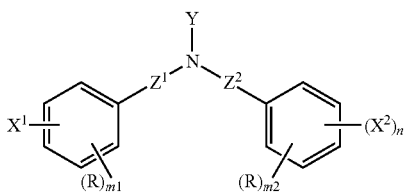

In the formula,
$X^1$ and $X^2$ each independently represent a C7 to C20 alkyl group or a C7 to C20 alkoxy group.

As the C7 to C20 alkyl group in $X^1$ and $X^2$, both a linear C7 to C20 alkyl group and a branched C7 to C20 alkyl group may be preferably used.

As the linear C7 to C20 alkyl group, a n-heptyl group, a n-octyl group, a n-nonyl group, a n-decyl group, a n-dodecyl group, a n-tridecyl group, a n-tetradecyl group, a n-hexadecyl group, a n-octadecyl group, a n-eicosyl group, or the like may be exemplified.

As the branched C7 to C20 alkyl group, a 1,1,2,2-tetramethylpropyl group, a 1,1,3-trimethylbutyl group, an 1-ethylpentyl group, a 1,1,3,3-tetramethylbutyl group, a 2,2,3,3-tetramethylbutyl group, a 1,2,4-trimethylpentyl group, a 2,4,4-trimethylpentyl group, a 2,2,4-trimethylpentyl group, an 1-ethyl-4-methylpentyl group, an 3-ethyl-3-methylpentyl group, an 3-ethyl-4-methylpentyl group, an 1-ethyl-1-methylpentyl group, a 1,1-dimethylhexyl group, a 3,3-dimethylhexyl group, a 4,4-dimethylhexyl group, an 2-ethylhexyl group, an 3-ethylhexyl group, a 6-methylheptyl group, a 1,3,5-trimethylhexyl group, a 1,1,3-trimethylhexyl group, a 1-butyl-1-methylheptyl group, a 1-methylheptyl group, a 1-methyl-1-octylundecyl group, or the like may be exemplified.

As the C7 to C20 alkoxy group in $X^1$ and $X^2$, both a linear C7 to C20 alkoxy group and a branched C7 to C20 alkoxy group may be preferably used.

As the linear C7 to C20 alkoxy group, a n-heptyloxy group, a n-octyloxy group, a n-nonyloxy group, a n-decyloxy group, a n-dodecyloxy group, a n-tridecyloxy group, a n-tetradecyloxy group, a n-hexadecyloxy group, a n-octadecyloxy group, a n-eicosyloxy group, or the like may be exemplified.

As the branched C7 to C20 alkoxy group, a 1,1,2,2-tetramethylpropyloxy group, a 1,1,3-trimethylbutyloxy group, an 1-ethylpentyloxy group, a 1,1,3,3-tetramethylbutyloxy group, a 2,2,3,3-tetramethylbutyloxy group, a 1,2,4-trimethylpentyloxy group, a 2,4,4-trimethylpentyloxy group, a 2,2,4-trimethylpentyloxy group, an 1-ethyl-4-methylpentyloxy group, an 3-ethyl-3-methylpentyloxy group, an 3-ethyl-4-methylpentyloxy group, an 1-ethyl-1-methylpentyloxy group, a 1,1-dimethylhexyloxy group, a 3,3-dimethylhexyloxy group, a 4,4-dimethylhexyloxy group, an 2-ethylhexyloxy group, an 3-ethylhexyloxy group, a 6-methylheptyloxy group, a 1,3,5-trimethylhexyloxy group, a 1,1,3-trimethylhexyloxy group, a 1-butyl-1-methylheptyloxy group, a 1-methylheptyloxy group, a 1-methyl-1-octylundecyloxy group, or the like may be exemplified.

In the formula, n represents 0 or 1.
In the formula, $Z^1$ and $Z^2$ each independently represent a single bond or a C1 to C3 alkylene group.

As the C1 to C3 alkylene group in $Z^1$ and $Z^2$, methylene, ethylene, propane-1,3-diyl, or the like may be exemplified.

In the formula, R represents an organic group or a halogeno group.

The organic group or the halogeno group is not particularly limited as long as it is chemically permitted and it has the effect of the present invention. As the organic group, a C1 to C6 alkyl group such as a methyl group, an ethyl group, a n-propyl group, an i-propyl group, a n-butyl group, a s-butyl group, an i-butyl group, a t-butyl group, a n-pentyl group, or a n-hexyl group; a C6 to C10 aryl group such as a phenyl group or a naphthyl group; a C1 to C6 alkoxy group such as a methoxy group, an ethoxy group, a n-propoxy group, an i-propoxy group, a n-butoxy group, a s-butoxy group, an i-butoxy group, or a t-butoxy group; a C1 to C6 haloalkyl group such as a chloromethyl group, a chloroethyl group, a trifluoromethyl group, a 1,2-dichloro-n-propyl group, a 1-fluoro-n-butyl group, or a perfluoro-n-pentyl group; or the like may be exemplified.

As the halogeno group, a fluoro group, a chloro group, a bromo group, an iodo group, or the like may be exemplified.

In the formula, m1 and m2 each independently represent any integer of 0 to 4.

In the formula, Y represents a polymerizable functional group. As the polymerizable functional group, a group or the like such as an acryloyl group, a methacryloyl group, a vinyloxycarbonyl group, a prop-1-en-2-yloxycarbonyl group, or an allyloxycarbonyl group having a polymerizable carbon-carbon double bond is exemplified.

In the present invention, as Y, an acryloyl group or a methacryloyl group is preferred.

The above formula (I) includes a compound of the following formula (II):

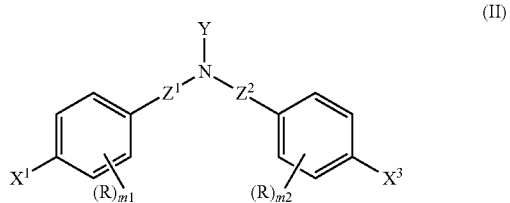

(II)

In the formula, Y, $Z^1$, $Z^2$, $X^1$, R, m1, and m2 represent the same as those explained in formula (I).

In the formula, $X^3$ represents a C7 to C20 alkyl group, a C7 to C20 alkoxy group, a hydrogen atom, an organic group, or a halogeno group. Of these, a C7 to C20 alkyl group or a C7 to C20 alkoxy group is preferred.

As the C7 to C20 alkyl group in $X^3$, the same as the C7 to C20 alkyl groups in $X^1$ and $X^2$ in formula (I) may be mentioned.

As the C7 to C20 alkoxy group in $X^3$, the same as the C7 to C20 alkoxy groups in $X^1$ and $X^2$ in formula (I) may be mentioned.

As the organic group and the halogeno group in $X^3$, the same as the organic groups and the halogeno groups in R in formula (I) may be mentioned.

Among polymerizable compounds of formula (I) or formula (II) used for the present invention, N,N-bis(4-(1,1,3,3-tetramethylbutyl)phenyl)acrylamide, N,N-bis(4-(1,1,3,3-tetramethylbutyl)phenyl)methacrylamide, N-phenyl-N-(4-(2,4,4-trimethylpentan-2-yl)phenyl)acrylamide, N-phenyl-N-(4-(2,4,4-trimethylpentan-2-yl)phenyl)methacrylamide, N,N-bis(4-octylphenyl)acrylamide, N,N-bis(4-octylphenyl)methacrylamide, N-(4-octylphenyl)-N-phenylacrylamide, or N-(4-octylphenyl)-N-phenylmethacrylamide is exemplified preferably.

The polymerizable compounds of formula (I) or formula (II) used for the present invention may be obtained by the methods of the examples or other known synthesizing methods.

For example, when Y in formula (I) is an acryl group or a methacryl group, the polymerizable compound may be manufactured by the following method.

A secondary amine of formula (I')

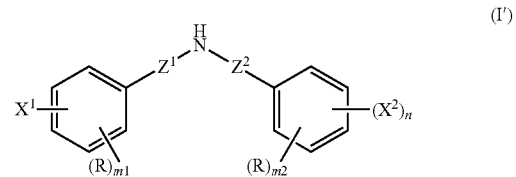

(I')

(wherein $X^1$, $X^2$, n, $Z^1$, $Z^2$, R, m1, and m2 have the same definitions as in formula (I)) and a (meth)acryloyl halide such as (meth)acryloyl chloride are allowed to react in the presence of a base in a solvent.

As the solvent, an amide-based solvent such as N,N-dimethylformamide (DMF) or N,N-dimethylacetamide; an ether-based solvent such as tetrahydrofuran (THF), 1,2-dimethoxyethane, diethyl ether, or methyl cellosolve; an aromatic hydrocarbon such as benzene, toluene, xylene, chlorobenzene, dichlorobenzene, or benzonitrile; a saturated hydrocarbon such as pentane, hexane, octane, or cyclohexane; a halogenated hydrocarbon such as dichloromethane, chloroform, carbon tetrachloride, or 1,2-dichloroethane, or the like may be exemplified, and one of these solvents or a mixed solvent of two or more thereof may be used.

As the base, an organic base such as an aliphatic amine such as triethylamine or tributylamine; an aromatic amine such as pyridine, N-ethylpyridine, N,N-dimethylaniline, or N,N-dimethylaminopyridine; or a metal alkoxide such as sodium ethylate or sodium methylate; or an inorganic base such as a hydroxide of an alkali metal or an alkaline earth metal or a carbonate of an alkali metal or alkaline earth metal such as lithium hydroxide, sodium hydroxide, potassium hydroxide, lithium carbonate, sodium carbonate, potassium carbonate, calcium hydroxide, magnesium hydroxide, calcium carbonate, magnesium carbonate, or sodium bicarbonate may be used.

The reaction temperature is −50 to 200° C.

The polymer used in the present invention is not particularly limited as long as it is obtained by polymerizing a polymerizable compound of formula (I). The polymerization reaction is not particularly limited, and may be a known method for synthesizing a polyacrylate or the like. For example, radical polymerization, anionic polymerization, coordinated polymerization, or the like may be exemplified. One example thereof is shown in Examples.

For example, when a compound in which Y in formula (I) is an acryl group or a methacryl group is polymerized by a radical polymerization, a polymerizable compound of formula (I) or formula (II) is polymerized by heating or light irradiation in the presence of a radical polymerization initiator in a solvent.

The solvent for polymerization is not reacted in a polymerization reaction and is not particularly limited as long as it is a solvent compatible with a polymer. Specifically, as the solvent for polymerization, a nonpolar solvent or a low polarity solvent such as an ether-based compound such as diethyl ether, tetrahydrofuran (THF), dioxane, or trioxane; an ester-based compound such as ethyl acetate; a ketone-based compound such as methyl ethyl ketone or cyclohexanone; an aliphatic, aromatic, or alicyclic hydrocarbon compound such as hexane or toluene, or the like may be exemplified. These solvents may be used alone or may be used as a mixed solvent of two or more thereof.

As the radical polymerization initiator, azobisisobutyronitrile, azobis-2,4-dimethylvaleronitrile, azobiscyclohexanecarbonitrile, azobis-2-amidinopropane hydrochloride, potassium peroxodisulphate, ammonium peroxodisulfate, t-butyl hydroperoxide, di-t-butyl cumene hydroperoxide peroxide, acetyl peroxide, benzoyl peroxide, lauroyl peroxide, or the like may be exemplified. The molecular weight of the polymer used in the present invention is not limited as long as it is in a range in which coating onto a substrate is possible. For example, a polymer having a number average molecular weight in the range of 1,000 to 1,000,000, 5,000 to 500,000, 10,000 to 200,000, or the like may be exemplified.

The molecular weight distribution (PDI) of the polymer according to the present invention is the ratio of the weight average molecular weight/the number average molecular weight (Mw/Mn), preferably 1.0 to 5.0, more preferably 1.0 to 4.0, and most preferably 1.0 to 3.0.

The weight average molecular weight and the number average molecular weight are values obtained by converting data measured by gel permeation chromatography (GPC) using THF as a solvent based on the molecular weight of polymethylmethacrylate used as a standard.

The polymer used for the present invention may be a linear polymer, a graft polymer, or a star polymer. When the polymer is a copolymer comprising a repeating unit derived from a polymerizable compound other than the repeating unit derived from the polymerizable compound of formula (I), it may be a random copolymer or a block copolymer.

The polymer used for the present invention may be a polymer having the repeating unit derived from the polymerizable compound of formula (I), and may be a copolymer having a repeating unit derived from a polymerizable compound other than the polymerizable compound of formula (I) such as a repeating unit derived from a (meth)acrylate monomer, a repeating unit derived from a (meth)acrylamide, a repeating unit derived from an aromatic vinyl monomer, or a repeating unit derived from an olefin monomer.

When the copolymer comprises a repeating unit derived from a polymerizable compound other than the polymerizable compound of formula (I), the polymer preferably contains 30% by weight or more of the repeating unit derived from the polymerizable compound of formula (I), a polymer containing 50% by weight or more thereof is more preferred, and a polymer containing 70% by weight or more thereof is further preferred. A homopolymer obtained by polymerizing one polymerizable compound of formula (I), or a polymer obtained by polymerizing two or more polymerizable compounds of formula (I) may also be preferably used.

As the polymerizable compound other than the polymerizable compound of formula (I), specifically, a (meth)acrylate such as methyl(meth)acrylate, ethyl(meth)acrylate, n-propyl(meth)acrylate, butyl(meth)acrylate, i-butyl(meth)acrylate, n-hexyl(meth)acrylate, 2-ethylhexyl(meth)acrylate, decyl(meth)acrylate, lauryl(meth)acrylate, stearyl(meth)acrylate, cyclohexyl(meth)acrylate, or trityl(meth)acrylate; a (meth)acrylamide such as dimethyl(meth)acrylamide, diethyl(meth)acrylamide, (meth)acryloylmorpholine, hydroxyethyl(meth)acrylamide, or isopropyl(meth)acrylamide; a vinyl compound such as styrene, vinyl acetate, vinyl chloride, vinylidene chloride, acrylonitrile, vinyl ether, acrolein, or divinylbenzene; or an olefin compound such as ethylene, propylene, or butadiene, or the like is exemplified.

[Other Components]
(Organic Solvent)

An organic solvent may be comprised in the adhesive composition of the present invention. As a typical organic solvent that may be used, an ether-based organic solvent, an ester-based organic solvent, an aliphatic hydrocarbon-based organic solvent, an aromatic hydrocarbon-based organic solvent, a ketone-based organic solvent, an organohalide-based organic solvent, or the like is exemplified.

As the ether-based organic solvent, diethyl ether, dipropyl ether, dibutyl ether, diamyl ether, or the like is exemplified; as the ester-based organic solvent, ethyl acetate, propyl acetate, butyl acetate, amyl acetate, heptyl acetate, ethyl butyrate, isoamyl isovalerate, or the like is exemplified; as the aliphatic hydrocarbon-based organic solvent, normal hexane, normal heptane, cyclohexane, or the like is exemplified; as the aromatic hydrocarbon-based organic solvent, toluene, xylene, or the like is exemplified; as the ketone-based organic solvent, methyl ethyl ketone, methyl isobutyl ketone, cyclohexanone, or the like is exemplified; and as the organohalide-based organic solvent, trichloroethane, trichloroethylene, or the like is exemplified. Further, a relatively inactive organic solvent such as propylene glycol monomethyl ether or propylene glycol monoethyl ether may also be used.

Especially, an ester-based organic solvent such as propyl acetate, butyl acetate, isoamyl acetate, heptyl acetate, ethyl butyrate, or isoamyl isovalerate is preferred.

(Polymerizable Compound Used with Polymer (I))

The adhesive composition of the present invention may solely comprise a polymerizable compound other than the polymerizable compound of formula (I), not as a copolymer component in polymer (I).

The polymerizable compound may be properly selected depending on target physical properties such as the melting point, viscosity, and the refractive index, and is not particularly limited, but specifically the following are exemplified:

A monofunctional (meth)acrylate such as methyl(meth)acrylate, ethyl(meth)acrylate, n-propyl(meth)acrylate, butyl(meth)acrylate, i-butyl(meth)acrylate, t-butyl(meth)acrylate, n-hexyl(meth)acrylate, 2-ethylhexyl(meth)acrylate, decyl(meth)acrylate, lauryl(meth)acrylate, stearyl(meth)acrylate, cyclohexyl(meth)acrylate, trityl(meth)acrylate, isobornyl(meth)acrylate, tetrahydrofurfuryl(meth)acrylate, or hydroxyethyl(meth)acrylate;

a bifunctional (meth)acrylate such as ethylene glycol di(meth)acrylate, diethylene glycol di(meth)acrylate, triethylene glycol di(meth)acrylate, polyethylene glycol di(meth)acrylate, propylene glycol di(meth)acrylate, dipropylene glycol di(meth)acrylate, polypropylene glycol di(meth)acrylate, propanediol di(meth)acrylate, glycerin di(meth)acrylate, cyclohexanediol di(meth)acrylate, bis[(meth)acryloxymethyl]cyclohexane, bisphenol A-di(meth)acrylate, or a di(meth)acrylate of an alkylene oxide adduct of bisphenol A; or a polyfunctional, trifunctional or higher, (meth)acrylate such as trimethylolpropane tri(meth)acrylate, pentaerythritol tetra(meth)acrylate, dipentaerythritol penta(meth)acrylate, or dipentaerythritol hexa(meth)acrylate;

a (meth)acrylamide such as dimethyl(meth)acrylamide, diethyl(meth)acrylamide, (meth)acryloylmorpholine, hydroxyethyl(meth)acrylamide, or isopropyl(meth)acrylamide;

An acrylic polymerizable oligomer such as epoxy (meth)acrylate, urethane (meth)acrylate, a polyester (meth)acrylate, a (meth)acrylate of a polybutadiene oligomer, a polyamide (meth)acrylic oligomer, melamine (meth)acrylate, a (meth)acrylate of a cyclopentadiene oligomer, a (meth) acrylate of a silicone oligomer.

A vinyl compound such as styrene, vinyl acetate, vinyl chloride, vinylidene chloride, acrylonitrile, vinyl ether, acrolein, or divinylbenzene; or an olefin compound such as ethylene, propylene, or butadiene.

As long as the adhesive properties and adhesiveness of the adhesive composition is not deteriorated, the added amount of the polymerizable compound is not limited.

(Polymerization Initiator)

The adhesive composition of the present invention may comprise a polymerization initiator. Here, as the polymerization reaction, a photopolymerization reaction, a thermal polymerization reaction, a radical polymerization, a redox reaction, or the like is exemplified.

As the photopolymerization initiator, (a) a compound that generates a cationic species by light irradiation, and (b) a compound that generates an active radical species by light irradiation, or the like may be exemplified.

As the compound that generates a cationic species by light irradiation, for example, an onium salt in which the cationic moiety is a sulfonium, iodonium, diazonium, ammonium, or (2,4-cyclopentadien-1-yl)[(1-methylethyl)benzene]-Fe cation, and the anionic moiety is composed of $BF_4-$, $PF_6-$, $SbF_6-$, or $[BX_4]-$ (X represents a phenyl group substituted by at least two or more fluorine atoms or a trifluoromethyl group) is exemplified.

Specifically, as the sulfonium salt, bis[4-(diphenylsulfonio)phenyl]sulfide bishexafluorophosphate, bis[4-(diphenylsulfonio)phenyl]sulfide bishexafluoroantimonate, bis[4-(diphenylsulfonio)phenyl]sulfide bistetrafluoroborate, bis[4-(diphenylsulfonio)phenyl]sulfide tetrakis(pentafluorophenyl)borate, diphenyl-4-(phenylthio)phenylsulfonium hexafluorophosphate, diphenyl-4-(phenylthio)phenylsulfonium hexafluoroantimonate, diphenyl-4-(phenylthio)phenylsulfonium tetrafluoroborate, diphenyl-4-(phenylthio)phenylsulfonium tetrakis(pentafluorophenyl)borate, triphenylsulfonium hexafluorophosphate, or the like is exemplified.

As the iodonium salt, diphenyliodonium hexafluorophosphate, diphenyliodonium hexafluoroantimonate, diphenyliodonium tetrafluoroborate, diphenyliodonium tetrakis(pentafluorophenyl)borate, bis(dodecylphenyl)iodonium hexafluorophosphate, bis(dodecylphenyl)iodonium hexafluoroantimonate, bis(dodecylphenyl)iodonium tetrafluoroborate, bis(dodecylphenyl)iodonium tetrakis(pentafluorophenyl)borate, or the like is exemplified.

As the diazonium salt, phenyldiazonium hexafluorophosphate, phenyldiazonium hexafluoroantimonate, phenyldiazonium tetrafluoroborate, phenyldiazonium tetrakis(pentafluorophenyl)borate, or the like is exemplified.

As the ammonium salt, 1-benzyl-2-cyanopyridinium hexafluorophosphate, 1-benzyl-2-cyanopyridinium hexafluoroantimonate, 1-benzyl-2-cyanopyridinium tetrafluoroborate, 1-benzyl-2-cyanopyridinium tetrakis(pentafluorophenyl)borate, 1-(naphthylmethyl)-2-cyanopyridinium hexafluorophosphate, 1-(naphthylmethyl)-2-cyanopyridinium hexafluoroantimonate, 1-(naphthylmethyl)-2-cyanopyridinium tetrafluoroborate, 1-(naphthylmethyl)-2-cyanopyridinium tetrakis(pentafluorophenyl)borate, or the like is exemplified.

As the (2,4-cyclopentadien-1-yl)[(1-methylethyl)benzene]-Fe salt, (2,4-cyclopentadien-1-yl) [(1-methylethyl)benzene]-Fe(II) hexafluorophosphate, (2,4-cyclopentadien-1-yl)[(1-methylethyl)benzene]-Fe(II) hexafluoroantimonate, (2,4-cyclopentadien-1-yl)[(1-methylethyl)benzene]-Fe(II) tetrafluoroborate, (2,4-cyclopentadien-1-yl)[(1-methylethyl)benzene]-Fe(II) tetrakis(pentafluorophenyl)borate, or the like is exemplified.

As the compound that generates an active radical species by light irradiation, specifically, acetophenone, acetophenone benzyl ketal, 1-hydroxycyclohexyl phenyl ketone, 2,2-dimethoxy-1,2-diphenylethan-1-one, xanthone, fluorenone, benzaldehyde, fluorene, anthraquinone, triphenylamine, carbazole, 3-methylacetophenone, 4-chlorobenzophenone, 4,4'-dimethoxybenzophenone, 4,4'-diaminobenzophenone, benzoin propyl ether, benzoin ethyl ether, benzyl dimethyl ketal, 1-(4-isopropylphenyl)-2-hydroxy-2-methylpropan-1-one, 2-hydroxy-2-methyl-1-phenylpropan-1-one, thioxanthone, diethylthioxanthone, 2-isopropylthioxanthone, 2-chlorothioxanthone, 2-methyl-1-[4-(methylthio)phenyl]-2-morpholino-propan-1-one, 2-benzyl-2-dimethylamino-1-(4-morpholinophenyl)-butanone-1,4-(2-hydroxyethoxy) phenyl-(2-hydroxy-2-propyl) ketone, 2,4,6-trimethylbenzoyldiphenylphosphine oxide, bis-(2,6-dimethoxybenzoyl)-2,4,4-trimethylpentylphosphine oxide, oligo(2-hydroxy-2-methyl-1-(4-(1-methylvinyl)phenyl)propanone), or the like is exemplified.

The thermal polymerization initiator refers to a compound that generates a radical by heating, and an organic peroxide, an azo compound, and a redox initiator, or the like is exemplified.

For the blended amount of the polymerization initiator used in the present invention, 0.01 to 20% by weight of the polymerization initiator is preferably blended, and 0.1 to 10% by weight is further preferred with respect to the total amount of all polymerizable compounds.

[Provision of Functionality]

(Condensate of Organosilane Compound)

A condensate of an organosilane compound may be comprised in the adhesive composition of the present invention for the purpose of mineralizing the surface of a coating film. Thus, a glassy hard coat layer may be layered on the surface of a plastic substrate. The method for preparing the condensate of the organosilane compound is described in, for example, WO2018/070079.

(Metal Compound and the Like)

A metal compound may be added to the adhesive composition of the present invention for the purpose of increasing the refractive index and the hardness of the coating film. As the metal compound, the above-described organosilane compound, and the organic metal, the organic acid metal salt, the metal hydroxide, and the metal complex exemplified as the silanol condensation catalyst are exemplified. As a metal compound other than these, a metal oxide is exemplified, and specifically, particles of a metal oxide that is silicon dioxide, titanium oxide, aluminum oxide, chromium oxide, manganese oxide, iron oxide, zirconium oxide (zirconia), or cobalt oxide, or the like are exemplified. Particularly zirconium oxide is preferred.

As the shape of the particles, a spherical form, a porous powder form, a scaly form, a fibrous form, or the like is exemplified, and the shape of the particles is more preferably a porous powder form.

As the metal oxide particles of the present invention, colloidal metal oxide particles may also be used. Specifically, colloidal silica and colloidal zirconium may be exemplified, and water-dispersed colloidal metal oxide particles or colloidal metal oxide particles dispersed in an organic solvent such as methanol or isopropanol may be exemplified.

For the development of properties such as the coloration of the coating film, film thickening, the prevention of the transmission of ultraviolet rays, the provision of anticorrosiveness, and the heat resistance, a filler may also be separately added and dispersed. As the filler, a water-insoluble pigment such as an organic pigment or an inorganic pigment, a particulate, fibrous, or scaly metal and alloy and oxide, hydroxide, carbide, nitride, and sulfide thereof other than a pigment, or the like are exemplified.

In addition, additives such as a known dehydrating agent such as methyl orthoformate, methyl orthoacetate, or tetraethoxysilane, various surfactants, and a silane coupling agent, a titanium coupling agent, a dye, a dispersing agent, a thickening agent, and a leveling agent other than the above may also be added.

In the present invention, additive components such as a sensitizer, an ultraviolet absorbing agent, a dye, a rust preventive, and a preservative may be blended as required.

The adhesive composition of the present invention may be used by mixing it with an existing adhesive.

[Preparation of Adhesive Composition]

The adhesive composition in the present invention is usually prepared by mixing, in addition to the polymer (I), the above polymerizable compound, the above condensate of the organosilane compound, a photopolymerization initiator, a metal compound, and the like as required, in an organic solvent. The solid content of the adhesive composition of the present invention is preferably 1 to 90% by weight, and more preferably 5 to 60% by weight.

2. Molded Body

The molded body of the present invention is a molded body in which a film (coating film) obtained by coating the above adhesive composition to a plastic substrate, and curing the above adhesive composition is provided directly on the substrate.

[Substrate]

As the substrate on which the adhesive composition of the present invention may be used, a plastic substrate is preferred, and, specifically, a cycloolefin resin such as a cycloolefin homopolymer or a cycloolefin copolymer; a polyolefin such as polyethylene, polypropylene, polyisoprene, polybutadiene, polymethylpentene; a polycarbonate; a polyisocyanate; a polyimide; a polyester; an acrylic resin; a methacrylic resin; an epoxy resin; a polyethylene terephthalate; or an aromatic polyether ketone or the like is exemplified.

Particularly a polyethylene and a polypropylene are preferably used.

[Formation of Coating Film]

The polymer (I) in the adhesive composition of the present invention firmly adheres to the surface of a substrate. Therefore, a coating film may be formed if only the adhesive composition is heat-dried after application. When the adhesive composition further comprises a polymerizable compound, ultraviolet irradiation treatment using the photopolymerization initiator in combination or heat treatment using the thermal polymerization initiator in combination is preferably performed.

Since the surface of the substrate does not need to be modified by UV-ozone treatment or the like, the inherent characteristics of the plastic substrate may be maintained.

As the method for coating the adhesive composition, a known coating method may be used, and a dipping method, a spraying method, a bar coating method, a roll coating method, a spin coating method, a curtain coating method, a gravure printing method, a silk screen method, an ink jet method, or the like is exemplified. The thickness of the formed coating film is not particularly limited, and is about 0.1 to 200 μm.

The heating and drying treatment of the coating film is preferably performed at 40 to 200° C. for about 0.5 to 120 minutes, and more preferably at 60 to 120° C. for about 1 to 60 minutes.

The irradiation with ultraviolet rays may be performed using a known apparatus such as a high pressure mercury lamp, a low pressure mercury lamp, a metal halide lamp, or an excimer lamp.

Heat treatment may be performed sequentially with drying treatment.

[Lamination of Functional Film]

Since the coating film of the present invention has very good adhesiveness to a plastic substrate, the coating film of the present invention may be used as a primer layer. Therefore, a functional film that may not be conventionally formed directly on a plastic substrate may be laminated via the coating film of the present invention. A plurality of layers may be laminated, and also a layer or layers may further be laminated by further applying the coating agent of the present invention to the plurality of layers.

As the functional film, a conductive film, an antireflection film, a gas barrier film, a hard coat film, a water-repellent film, a hydrophilic film, or the like is exemplified.

As the conductive film, a film of indium oxide doped with tin (ITO film), a film of tin oxide doped with fluorine (FTO film), a film of zinc oxide doped with antimony, a film of zinc oxide doped with indium, or the like is exemplified.

The gas barrier film is not particularly limited as long as it has gas barrier properties against oxygen, water vapor, and the like, and the gas barrier film is preferably a thin film of an inorganic compound, and particularly a thin film of a metal oxide, a metal nitride, or a metal carbide having a metal element selected from the group consisting of titanium, zirconium, aluminum, silicon, germanium, indium, tin, tantalum, zinc, tungsten, and lead, or a composite thereof is preferred.

The thickness of these functional films is usually 10 to 300 nm, preferably 10 to 200 nm, and more preferably 10 to 100 nm.

For the method for forming a conductive film, a gas barrier film, or the like, consisting of an inorganic compound on the coating film of the present invention, the conductive film or the gas barrier film may be formed by a known method, and the formation may be performed by a physical method such as a sputtering method, a vacuum deposition method, or an ion plating method, a chemical method such as a spraying method, a dipping method, a thermal CVD method, or a plasma CVD method, or the like.

For example, according to a sputtering method or the like, a film consisting of silicon oxide may also be formed by using as a target a sintered body obtained by sintering a silicon compound in the presence of oxygen gas, or the like, or a film may also be formed by reactively sputtering metal silicon as a target in the presence of oxygen. According to a plasma CVD method, a film consisting of silicon oxynitride on a substrate may be formed by supplying silane gas together with oxygen gas and nitrogen gas into a chamber in which a plasma is generated, to react them. According to a thermal CVD method or the like, a film consisting of silicon oxide may be formed by using as an evaporant an organic solvent solution containing a silicon compound, or the like.

In the present invention, the functional film is preferably formed particularly by a sputtering method, a vacuum deposition method, an ion plating method, or a plasma CVD method. When the functional film is formed, the surface of the coating film of the present invention may be previously plasma-treated or UV-ozone-treated as required.

The coating film of the present invention may also be used as an adhesive layer used when plastic substrates, or a plastic substrate and another formed sheet are adhered.

As the formed sheet, a plastic sheet consisting of a material such as polyvinyl chloride, a cellulose resin, polyethylene, polystyrene, an ABS resin, polyamide, polyester, polyurethane, or a cycloolefin resin; an optical film such as a polarizing plate, a phase difference film, or an antireflection film; metallic foil such as aluminum, copper, or silicon; or the like may be exemplified.

Examples will be shown below, but the technical scope of the present invention is not limited by these Examples.

EXAMPLES

The measurement of the number average molecular weights of polymers obtained in Examples was performed with the following device under the following conditions.
[Device]
Sample injector: Waters 2695 Alliance
Separation column: Shodex KF-G, 805L, 804L, 804L Detector: Waters 2414 refractive index (RI) detector, 2998 Photodiode array (PDA) detector
Column oven: column oven manufactured by Nihon Waters K.K.
[Conditions]
Column oven temperature: 40° C.
RI detector temperature: 40° C.
Mobile phase: tetrahydrofuran
Flow rate: 1.0 mL/min
Standard injection rate: 200 μL
PDA detector extraction wave: 254.0 nm
Quantitative calculation: in terms of standard polymethyl methacrylate Synthesis Example 1

Synthesis of N,N-bis(4-(1,1,3,3-tetramethylbutyl) phenyl)acrylamide (Compound A)

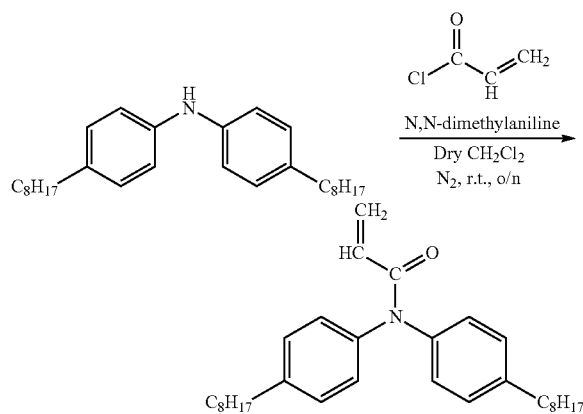

Bis[4-(1,1,3,3-tetramethylbutyl)phenyl]amine (NOCRAC AD-F manufactured by Ouchi Shinko Chemical Industrial Co., Ltd., containing a trace amount of N-phenyl-4-(1,1,3,3-tetramethylbutyl)benzenamine) (50.00 g, 0.127 mol), N,N-dimethylaniline (46.17 g, 0.381 mol), and 477 mL of super-dehydrated dichloromethane were added to a 1 L four-necked flask purged with nitrogen, and the mixture was stirred until the components were dissolved uniformly. Then, the reaction solution was cooled to 0° C. or less in an ice/ethanol bath, acrylic acid chloride (22.99 g, 0.254 mol) was slowly dropped, and the mixture was stirred for 30 minutes. Then, the temperature of the reaction liquid was increased to room temperature, and the reaction was performed for 24 hours. After the completion of the reaction, the solvent was distilled off by an evaporator, and the crude product was dissolved in 250 mL of ethyl acetate. Then, the reaction solution was water-washed with 1 N aqueous hydrochloric acid solution, saturated sodium bicarbonate water, and salt solution. The organic layer was dried over magnesium sulfate and then the filtrate was distilled off by an evaporator. The obtained crude product was recrystallized and purified with hexane to obtain N,N-bis(4-(1,1,3,3-tetramethylbutyl)phenyl)acrylamide (Compound A, 38.67 g, yield 68%). The result of mass spectrometry is shown below.

By NMR of High Resolution ESI-TOF-MS m/z Calcd. for $[C_{31}H_{45}NO\ ([M+Na]^+)]$: 470.3393 found 470.3317, containing 100% N,N-bis(4-(1,1,3,3-tetramethylbutyl)phenyl) acrylamide was confirmed.

$^1$H NMR (500 MHz, chloroform-$d_1$, TMS): δ/ppm=7.33, 7.12, 6.43, 6.16, 5.56, 1.72, 1.35, 0.72

Synthesis Example 2

Making of poly{N,N-bis(4-(1,1,3,3-tetramethylbutyl) phenyl)acrylamide} (Compound A-1)

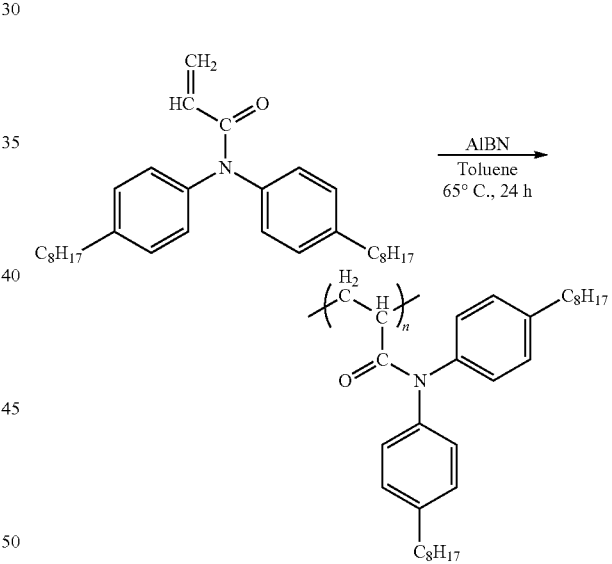

10.00 g of N,N-bis(4-(1,1,3,3-tetramethylbutyl)phenyl) acrylamide obtained in Synthesis Example 1 and 0.030 g of azobisisobutyronitrile were added to a 200 mL two-neck flask. A stirring bar was placed, and the Schlenk tube was sealed with a three-way cock, and then a gas sampling bag containing nitrogen was placed. The container was degassed by a vacuum pump, and then purged with nitrogen. Then, 40.00 mL of deoxygenated toluene was added, and the mixture was heated in an oil bath at 65° C. for 24 hours, resulting in a radical polymerization reaction. After the completion of the reaction, the reaction liquid was added to methanol for reprecipitation. From GPC, the number average molecular weight ($M_n$) of the obtained polymer was 23,700, and the molecular weight distribution (PDI) was 1.88.

Synthesis Examples 3 to 7

As in Synthesis Example 2, poly{N,N-bis(4-(1,1,3,3-tetramethylbutyl)phenyl)acrylamide} of different molecular weights (Compounds A-2 to A-6) were made by thermal radical polymerization reaction using azobisisobutyronitrile (AIBN) as an initiator. Table 1 shows the reaction conditions and the yields, number average molecular weight, and molecular weight distribution of the obtained high molecular weight compounds.

TABLE 1

| Compound | Compound A(g) | Amount of toluene (g) | AIBN (g) | Yield (%) | Number average molecular weight $M_n$ | Molecular weight distribution |
|---|---|---|---|---|---|---|
| A-1 | 10 | 34.67 | 0.030 | 32 | 23,700 | 1.88 |
| A-2 | 30 | 45.00 | 0.077 | 61 | 19,128 | 1.71 |
| A-3 | 30 | 45.00 | 0.097 | 95 | 14,316 | 1.89 |
| A-4 | 30 | 45.00 | 0.193 | 95 | 13,327 | 1.53 |
| A-5 | 30 | 70.00 | 0.242 | 98 | 11,178 | 1.42 |
| A-6 | 30 | 70.00 | 0.386 | 97 | 6,356 | 1.56 |

(Solubility Test)

The solubility of Compounds A-1 to A-6 and poly(N,N-diphenylacrylamide) (Compound B) in various reagents was investigated. With 0.7 g of a reagent was mixed 0.3 g each of Compounds A-1 to A-6 and Compound B, and the mixture was stirred with a stirring bar for 20 minutes. The extent of dissolution was examined visually. If there was no undissolved residue, complete dissolution (○) was determined. If there were undissolved residues, insolubility (×) was determined. The results are shown in Table 2.

The used reagents are shown below.

n-Hexane
Toluene
Tetrahydrofuran
Cyclohexanone
Ethyl acetate
Methyl acrylate (MA)
Ethyl acrylate (EA)
n-Butyl acrylate (nBA)
Cyclohexyl acrylate (CHA)
Isobornyl acrylate (IBOA)
2-Ethylhexyl acrylate (EHA)
Tetrahydrofurfuryl acrylate (THFA)
Epoxy resin (YD-128)

TABLE 2

| Results of Solubility Test | | | | | | | |
|---|---|---|---|---|---|---|---|
| | A-1 | A-2 | A-3 | A-4 | A-5 | A-6 | B |
| n-Hexane | ○ | ○ | ○ | ○ | ○ | ○ | × |
| Toluene | ○ | ○ | ○ | ○ | ○ | ○ | ○ |
| Tetrahydrofuran | ○ | ○ | ○ | ○ | ○ | ○ | ○ |
| Cyclohexanone | ○ | ○ | ○ | ○ | ○ | ○ | ○ |
| Ethyl acetate | ○ | ○ | ○ | ○ | ○ | ○ | × |
| MA | × | × | × | × | ○ | ○ | × |
| EA | × | × | ○ | ○ | ○ | ○ | × |
| nBA | ○ | ○ | ○ | ○ | ○ | ○ | × |
| CHA | ○ | ○ | ○ | ○ | ○ | ○ | × |
| IBOA | ○ | ○ | ○ | ○ | ○ | ○ | × |
| EHA | ○ | ○ | ○ | ○ | ○ | ○ | × |
| THFA | × | × | × | × | × | × | × |
| Epoxy resin | ○ | ○ | ○ | ○ | ○ | ○ | × |

Example 1

(1) Making of Coating Agent

In n-hexane was dissolved 1 g of poly{N,N-bis(4-(1,1,3,3-tetramethylbutyl)phenyl)acrylamide} (Compound A-1) obtained in Synthesis Example 2 at 10 wt %.

(2) Formation of Coating Film

Films of the coating agent were formed on various substrates of a size of 50×50 mm by bar coating. The coated substrates were heat-dried (at 80° C. for 5 minutes) in an oven to obtain formed bodies.

The used substrates are shown below.

Polyethylene plate (Wako, 1 mm)
Polypropylene plate (Wako, 1 mm)

(3) Cross-cut Peeling Test

To show that the coating agents of the present invention have excellent adhesiveness to substrates, the cross-cut peeling test of old JIS K5400 was performed on each of the formed bodies.

The evaluation results are represented by a fraction of the number of squares that are not peeled (numerator) to the number of all the squares (100 pieces) (denominator). 100/100 shows that none of the 100 squares are peeled.

The evaluation results showed 100/100 for all substrates. From the test result, it is found that the coating agents of the present invention have excellent adhesive properties.

Example 2

(1) Making of Adhesive (A)

First, 1.0 g of poly{N,N-bis(4-(1,1,3,3-tetramethylbutyl)phenyl)acrylamide} obtained in Synthesis Example 2 was dissolved in 1.0 g of THF to obtain an adhesive (A) having a solid concentration of 50 wt %.

(2) Making of Adhesiveness Test Sample

Two of various substrates of a size of 25×80×1.0 mm were adhered together in an area of 25×25 mm using 0.1 g of the above adhesive (A). The adhered part was fixed with a clip and heat-dried at 60° C. for 30 minutes to obtain an adhesiveness test sample.

The used substrates are shown below.

Polyethylene plate (Wako)
Polypropylene plate (Wako)

(3) Tensile Shear Peeling Test

A tensile shear peeling test was performed as an adhesiveness test. A SIMADZU AGS-J universal tensile tester comprising a load cell of 1 kN was used for the test. The device was equipped with an adhesiveness test sample, and the test was performed at a speed of 5 mm/min. The test was performed at room temperature. The adhesive strength of the adhesive (A) was 1.96 MPa for the polypropylene plate (PP) substrate and 1.54 MPa for the polyethylene plate (PE) substrate.

Comparative Example 1

(1) Making of Adhesive (B)

First, 1.0 g of poly(N,N-diphenylacrylamide) was dissolved in 1.0 g of THF to obtain an adhesive (B) having a solid concentration of 50 wt %.

(2) Making of Adhesiveness Test Sample

Two of various substrates of a size of 25×80×1.0 mm were adhered together in an area of 25×25 mm using 0.1 g of the above adhesive (B). The adhered part was fixed with a clip and heat-dried at 60° C. for 30 minutes to obtain an adhesiveness test sample.

The used substrates are shown below.
Polyethylene plate (Wako)
Polypropylene plate (Wako)

(3) Tensile Shear Peeling Test

The same tensile shear peeling test as for the adhesive (A) was performed as an adhesiveness test. The adhesive strength of the adhesive (B) was 0.51 MPa for the PP substrate and 0.66 MPa for the PE substrate.

From the test result, it is found that the adhesive of the present invention has excellent adhesive properties to polyethylene and polypropylene.

Example 3

(1) Making of Adhesive

First, 1.0 g each of Compounds A-1 to A-6 and Compound B was dissolved in 1.0 g of toluene to obtain an adhesive having a solid concentration of 50 wt %.

(2) Making of Adhesiveness Test Sample

Two substrates of various materials with a size of 25×100×2.0 mm were adhered together in an area of 25×25 mm using the above adhesive. The adhered part was fixed with a clip and heat-dried at 60° C. for 30 minutes to obtain an adhesiveness test sample.

The used substrates are shown below.

High density polyethylene (HDPE): Hitachi Chemical Co., Ltd., EL-N-AN

Polypropylene (PP): Hitachi Chemical Co., Ltd., PP-N-BN

Cycloolefin polymer (COP): ZEON Corporation, ZEONEX480R

Cycloolefin copolymer (COC): Mitsui Chemicals, Inc., APEL APL5014DP

Polymethylpentene (PMP): Mitsui Chemicals, Inc., TPX RT18

(3) Tensile Shear Peeling Test

A tensile shear peeling test was performed as an adhesiveness test. A SIMADZU AGS-J universal tensile tester comprising a load cell of 1 kN was used for the test. The device was equipped with an adhesiveness test sample, and the test was performed at a speed of 5 mm/min. The test was performed at room temperature. The results are shown in Table 3.

TABLE 3

Results of Tensile Shear Peeling Test

| Compound | PP | HDPE | COP | COC | PMP |
|---|---|---|---|---|---|
| A-1 | 1.96 | 1.54 | 2.44 | 2.62 | 2.09 |
| A-2 | 1.91 | 1.77 | 2.52 | 2.77 | 2.18 |
| A-3 | 2.09 | — | — | — | — |
| A-4 | 1.33 | — | — | — | — |
| A-5 | 1.09 | — | — | — | — |
| A-6 | 0.82 | — | — | — | — |
| B | 0.51 | — | — | — | — |

Example 4

(1) Making of Acrylic Resin Adhesive

Compounds A-1 to A-6 and Compound B were dissolved in a mixture of isobornyl acrylate (IBOA), 2-ethylhexyl acrylate (EHA), and Irgacure TPO (TPO) to obtain Acrylic Resin Adhesives 1 to 8. Table 4 shows the added amounts.

(2) Making of Adhesiveness Test Sample

Polycarbonate (PC) of a size of 25×100×2.0 mm and the following substrates of a size of 25×100×2.0 mm were adhered together in an area of 25×25 mm using the above adhesives. UV of a cumulative radiation dose of 2,000 mJ/cm$^2$ (Eye Graphics Co., Ltd., a belt conveyor-type ultraviolet ray irradiation apparatus UB044) was irradiated from the PC side to obtain an adhesiveness test sample.

The used substrates are shown below.

Polycarbonate (PC): Wako

High density polyethylene (HDPE): Hitachi Chemical Co., Ltd., EL-N-AN

Polypropylene (PP): Hitachi Chemical Co., Ltd., PP-N-BN

Cycloolefin polymer (COP): ZEON Corporation, ZEONEX480R

Cycloolefin copolymer (COC): Mitsui Chemicals, Inc., APEL APL5014DP

Polymethylpentene (PMP): Mitsui Chemicals, Inc., TPX RT18

(3) Tensile Shear Peeling Test

A tensile shear peeling test was performed as an adhesiveness test. A SIMADZU AGS-J universal tensile tester comprising a load cell of 1 kN was used for the test. The device was equipped with an adhesiveness test sample, and the test was performed at a speed of 100 ram/min. The test was performed at room temperature. The results are shown in Table 4.

TABLE 4

Adhesive Compositions and Results of Tensile Shear Peeling Test

| | | Acrylic resin adhesive | | | | | | | |
|---|---|---|---|---|---|---|---|---|---|
| | Material | 1 | 2 | 3 | 4 | 5 | 6 | 7 | 8 |
| Added amount of material (g) | A-1 | 0.600 | | | | | | | |
| | A-2 | | 0.600 | | | | | | |
| | A-3 | | | 0.600 | | | | | |
| | A-4 | | | | 0.600 | | | | |

TABLE 4-continued

Adhesive Compositions and Results of Tensile Shear Peeling Test

| | | Acrylic resin adhesive | | | | | | | |
|---|---|---|---|---|---|---|---|---|---|
| | Material | 1 | 2 | 3 | 4 | 5 | 6 | 7 | 8 |
| | A-5 | | | | | | 0.600 | | |
| | A-6 | | | | | | | 0.600 | |
| | B | | | | | | | | 0.600 |
| | IBOA | 1.500 | 1.200 | 1.200 | 1.200 | 1.200 | 1.200 | 1.200 | 1.200 |
| | EHA | 1.500 | 1.200 | 1.200 | 1.200 | 1.200 | 1.200 | 1.200 | 1.200 |
| | TPO | 0.120 | 0.096 | 0.096 | 0.096 | 0.096 | 0.096 | 0.096 | 0.096 |
| Tensile | PP | 0.23 | 1.88 | 1.59 | 2.03 | 1.30 | 0.73 | 0.64 | 0.68 |
| shear | HDPE | 0.65 | — | — | 1.67 | — | — | — | 0.88 |
| adhesive | COP | 0.57 | — | — | 1.94 | — | — | — | — |
| strength | COC | 0.88 | — | — | 2.03 | — | — | — | — |
| (MPa) | PMP | 0.18 | — | — | 1.59 | — | — | — | — |

Example 5

(1) Making of Adhesive

Compound A-2 was mixed with the following various adhesives to obtain adhesives 9 to 14. Table 5 shows the added amounts.

The used substrates are shown below.

Styrene-butadiene-rubber adhesive: Konishi Co., Ltd., Bond GP Clear

Silylated urethane resin adhesive: Konishi Co., Ltd., Bond Ultra Versatile SU Premium Soft Modified silicone resin adhesive: Cemedine Co., Ltd., Super X Hyper Wide (2) Making of Adhesiveness Test Sample The following substrates of a size of 25×100×2.0 mm were adhered together in an area of 25×25 mm using the above adhesives. The substrate was left and cured for one week to obtain an adhesiveness test sample.

The used substrates are shown below.

High density polyethylene (HDPE): Hitachi Chemical Co., Ltd., EL-N-AN

Polypropylene (PP): Hitachi Chemical Co., Ltd., PP-N-BN (3) Tensile Shear Peeling Test A tensile shear peeling test was performed as an adhesiveness test. A SIMADZU AGS-J universal tensile tester comprising a load cell of 1 kN was used for the test. The device was equipped with an adhesiveness test sample, and the test was performed at a speed of 100 ram/min. The test was performed at room temperature. The results are shown in Table 5.

TABLE 5

Adhesive Compositions and Results of Tensile Shear Peeling Test

| | | Adhesive | | | | | |
|---|---|---|---|---|---|---|---|
| | Material | 9 | 10 | 11 | 12 | 13 | 14 |
| Added amount | A-3 | | 0.60 | | 0.60 | | 0.60 |
| of material (g) | GP Clear | 3.00 | 2.40 | | | | |
| | SU | | | 3.00 | 2.40 | | |
| | Super X | | | | | 3.00 | 2.40 |
| Tensile shear | PP | 0.57 | 1.58 | 0.78 | 1.68 | 0.61 | 1.57 |
| adhesive | HDPE | 0.78 | 1.94 | 0.77 | 1.71 | 0.68 | 1.61 |
| strength (MPa) | | | | | | | |

From the test result, it is found that the adhesive composition of the present invention has excellent adhesive properties to polyethylene and polypropylene and high solubility (compatibility) with various solvents, and that adhesion can be further improved by mixing with a conventional adhesive.

The adhesive composition of the present invention may adhere to a wider variety of substrates and be available in composition forms of a wider variety.

The invention claimed is:

1. An adhesive composition, comprising a polymer having a repeating unit derived from a polymerizable compound of formula (I):

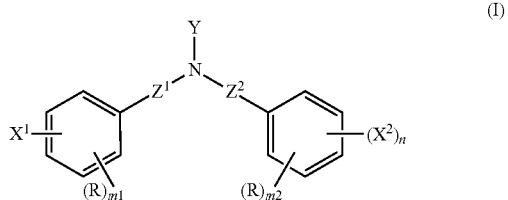

wherein:

$X^1$ and $X^2$ each independently represent a C7 to C20 alkyl group or a C7 to C20 alkoxy group;

n represents 0 or 1;

$Z^1$ and $Z^2$ each independently represent a single bond or a C1 to C3 alkylene group;

R each independently represents an organic group or a halogeno group;

m1 and m2 each independently represent any integer of 0 to 4; and

Y represents a polymerizable functional group.

2. The adhesive composition according to claim 1, wherein in formula (I), Y is an acryloyl group or a methacryloyl group.

3. The adhesive composition according to claim 1, wherein the polymerizable compound of formula (I) is a compound of formula (II):

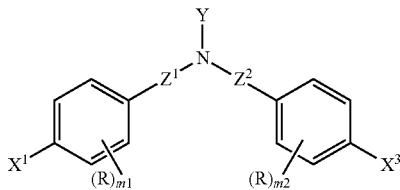

(II)

wherein:
$X^1$ represents a C7 to C20 alkyl group or a C7 to C20 alkoxy group;
$X^3$ represents a C7 to C20 alkyl group, a C7 to C20 alkoxy group, a hydrogen atom, an organic group, or a halogeno group;
$Z^1$ and $Z^2$ each independently represent a single bond or a C1 to C3 alkylene group;
R each independently represents an organic group or a halogeno group;
m1 and m2 each independently represent any integer of 0 to 4; and
Y represents a polymerizable functional group.

4. The adhesive composition according to claim 1, wherein the C7 to C20 alkyl group and the C7 to C20 alkoxy group are branched.

5. The adhesive composition according to claim 1, wherein the adhesive composition is an adhesive composition for a plastic substrate.

6. The adhesive composition according to claim 5, wherein the plastic substrate is a polyolefin substrate.

7. The adhesive composition according to claim 5, wherein the plastic substrate is a polypropylene substrate or a polyethylene substrate.

8. The adhesive composition according to claim 5, wherein the adhesive composition is a coating agent.

9. The adhesive composition according to claim 8, wherein the coating agent is a primer.

10. The adhesive composition according to claim 5, wherein the adhesive composition is an adhesive.

11. A molded body obtained by coating the adhesive composition according to claim 1 to a plastic substrate and curing the coated adhesive composition.

12. A compound of formula (II):

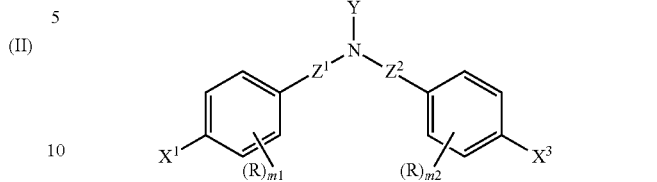

(II)

wherein:
$X^1$ and $X^3$ each independently represent a C7 to C20 alkyl group or a C7 to C20 alkoxy group;
$Z^1$ and $Z^2$ each independently represent a single bond or a C1 to C3 alkylene group;
R each independently represents an organic group or a halogeno group;
m1 and m2 each independently represent any integer of 0 to 4; and
Y represents a polymerizable functional group.

13. A polymer having a repeating unit derived from a polymerizable compound of formula (II):

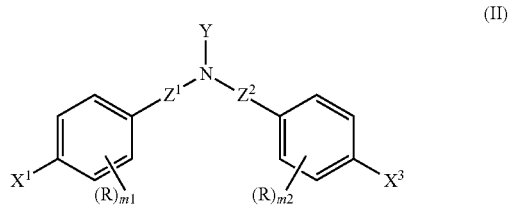

(II)

wherein:
$X^1$ and $X^3$ each independently represent a C7 to C20 alkyl group or a C7 to C20 alkoxy group; n represents 0 or 1;
$Z^1$ and $Z^2$ each independently represent a single bond or a C1 to C3 alkylene group;
R each independently represents an organic group or a halogeno group;
m1 and m2 each independently represent any integer of 0 to 4; and
Y represents a polymerizable functional group.

* * * * *

UNITED STATES PATENT AND TRADEMARK OFFICE
CERTIFICATE OF CORRECTION

| | |
|---|---|
| PATENT NO. | : 11,834,390 B2 |
| APPLICATION NO. | : 17/280931 |
| DATED | : December 5, 2023 |
| INVENTOR(S) | : Taiki Yamate |

It is certified that error appears in the above-identified patent and that said Letters Patent is hereby corrected as shown below:

In the Claims

Column 22, Lines 38-39, in Claim 13, Lines 6-7, "n represents 0 or 1;" should be deleted.

Signed and Sealed this
Twenty-sixth Day of March, 2024

Katherine Kelly Vidal
*Director of the United States Patent and Trademark Office*